(12) United States Patent
Blake et al.

(10) Patent No.: US 10,953,199 B2
(45) Date of Patent: Mar. 23, 2021

(54) DUAL DRESSING CATHETER SITE COVERING SYSTEM

(71) Applicants: Luke Blake, Bloomingdale, IN (US); Adam Schneider, Marshall, IL (US)

(72) Inventors: Luke Blake, Bloomingdale, IN (US); Adam Schneider, Marshall, IL (US)

( * ) Notice: Subject to any disclaimer, the term of this patent is extended or adjusted under 35 U.S.C. 154(b) by 43 days.

(21) Appl. No.: 16/175,912

(22) Filed: Oct. 31, 2018

(65) Prior Publication Data
US 2019/0070392 A1    Mar. 7, 2019

Related U.S. Application Data

(63) Continuation-in-part of application No. 15/802,528, filed on Nov. 3, 2017, and a continuation-in-part of application No. 15/377,146, filed on Dec. 13, 2016, now Pat. No. 10,117,717.

(51) Int. Cl.
*A61M 25/02* (2006.01)
*A61F 13/02* (2006.01)
*A61B 46/20* (2016.01)
*A61F 13/00* (2006.01)

(52) U.S. Cl.
CPC .......... *A61M 25/02* (2013.01); *A61B 46/20* (2016.02); *A61F 13/02* (2013.01); *A61F 13/023* (2013.01); *A61B 2046/205* (2016.02); *A61F 2013/00412* (2013.01); *A61M 2025/0246* (2013.01); *A61M 2025/0273* (2013.01)

(58) Field of Classification Search
CPC .......... A61B 46/00; A61B 2046/205; A61B 2046/234; A61B 2050/002; A61B 46/20; A61M 25/02

USPC .................................................. 604/385.05
See application file for complete search history.

(56) References Cited

U.S. PATENT DOCUMENTS

| | | | |
|---|---|---|---|
| 4,324,237 A | 4/1982 | Buttaravoli | |
| 4,875,473 A | 10/1989 | Alvarez | |
| 5,344,415 A | 9/1994 | deBusk et al. | |
| 5,395,675 A * | 3/1995 | Altholz | A61F 15/008 428/195.1 |
| 5,707,348 A | 1/1998 | Krogh | |
| 6,090,076 A | 7/2000 | Lane, Jr. | |
| 6,124,521 A | 9/2000 | Roberts | |
| 6,132,399 A | 10/2000 | Shultz | |
| 6,988,511 B2 | 1/2006 | Tang | |
| 7,612,248 B2 * | 11/2009 | Burton | A61F 13/0203 602/42 |

(Continued)

*Primary Examiner* — Deanna K Hall
(74) *Attorney, Agent, or Firm* — Reichel Stohry Dean LLP; Mark C. Reichel; Natalie J. Dean

(57) ABSTRACT

A dual dressing catheter site covering system prevents contamination of a wound site and inadvertent removal of a dressing from the catheter site. The system includes a primary dressing configured to cover a catheter site thereby inhibiting the catheter site from being contaminated. The primary dressing has an outer perimeter edge. A cover adhesive is positioned on a lower surface of a peripheral section of a cover dressing wherein the lower surface of the peripheral section adheres to the patient around the outer perimeter edge of the primary dressing. A central section of the cover dressing extends over and covers the primary dressing such that the cover dressing prevents contamination of the primary dressing.

19 Claims, 4 Drawing Sheets

(56) References Cited

U.S. PATENT DOCUMENTS 8,029,479 B2    10/2011  Guthrie
9,668,822 B2 *  6/2017  Czajka, Jr. ............. A61B 46/00

* cited by examiner

DUAL DRESSING CATHETER SITE COVERING SYSTEM

CROSS-REFERENCE TO RELATED APPLICATIONS

This application is a continuation in part of application Ser. No. 15/802,528 filed Nov. 3, 2017, and application Ser. No. 15/377,146 filed on Dec. 13, 2016.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to dressing devices and more particularly pertains to a new dressing device for preventing contamination of a catheter site and inadvertent removal of a dressing from the catheter site.

BRIEF SUMMARY OF THE INVENTION

An embodiment of the disclosure meets the needs presented above by generally comprising a primary dressing configured to cover a catheter site thereby inhibiting the catheter site from being contaminated. The primary dressing has an outer perimeter edge. A cover adhesive is positioned on a lower surface of a peripheral section of a cover dressing wherein the lower surface of the peripheral section adheres to the patient around the outer perimeter edge of the primary dressing. A central section of the cover dressing extends over and covers the primary dressing such that the cover dressing prevents contamination of the primary dressing.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
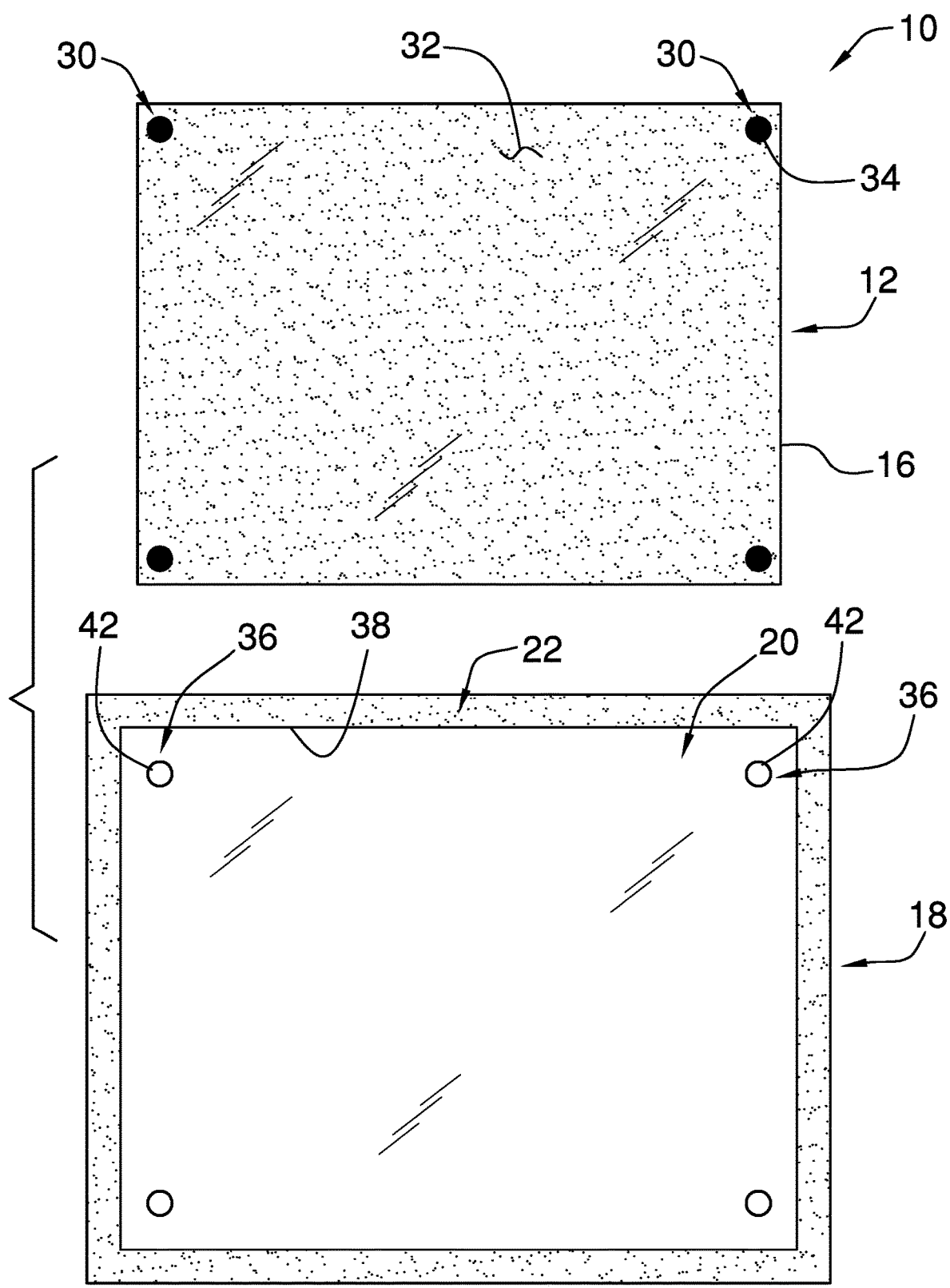
FIG. 1 is a top view of a dual dressing catheter site covering system according to an embodiment of the disclosure.
Figure 2:
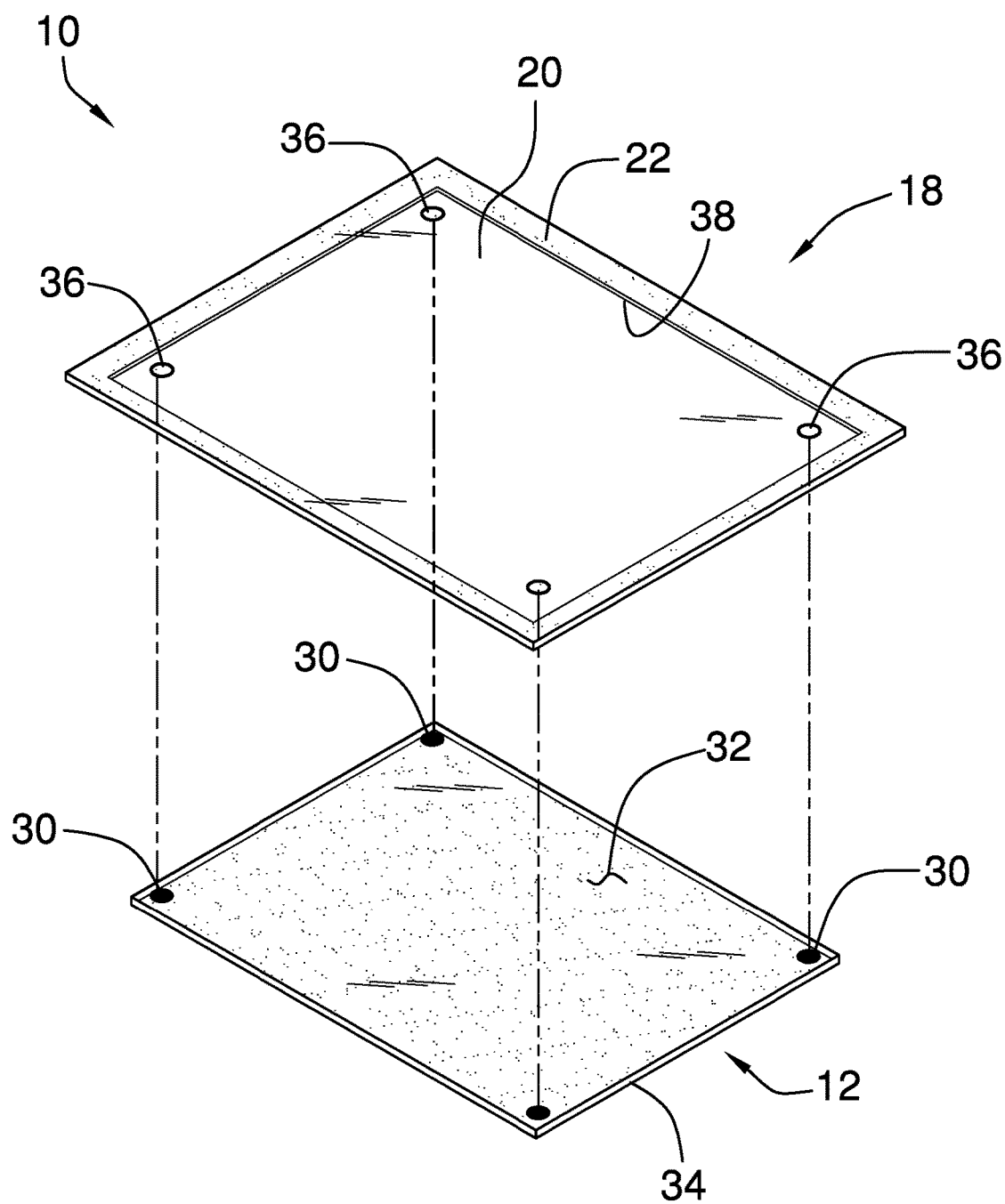
FIG. 2 is an exploded top front side perspective view of an embodiment of the disclosure.
Figure 3:
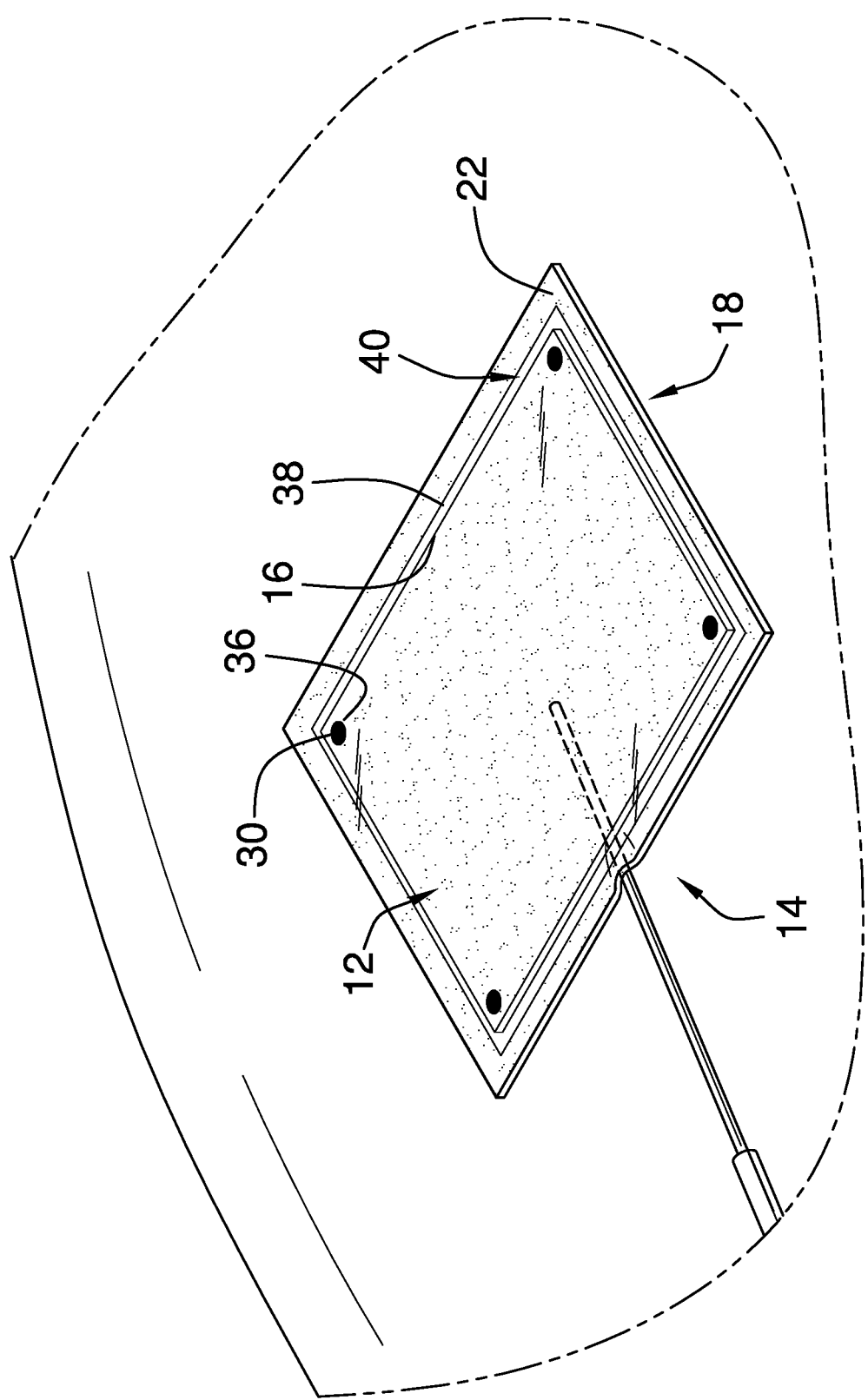
FIG. 3 is a top front side perspective view of an embodiment of the disclosure in use.
Figure 4:
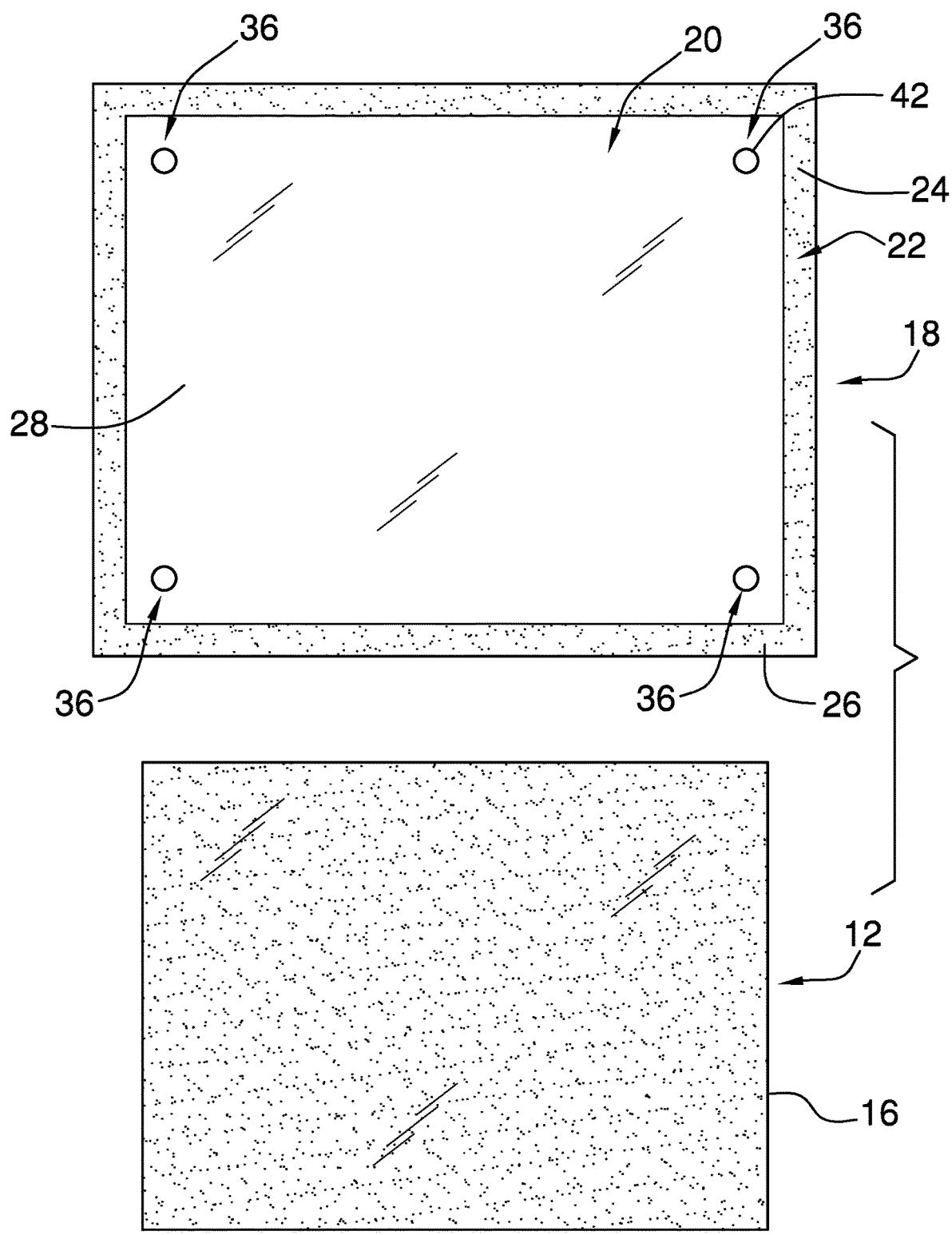
FIG. 4 is a bottom view of an embodiment of the disclosure.

With reference now to the drawings, and in particular to FIGS. 1 through 4 thereof, a new dressing device embodying the principles and concepts of an embodiment of the disclosure and generally designated by the reference numeral 10 will be described.

As best illustrated in FIGS. 1 through 4, the dual dressing catheter site covering system 10 generally comprises a primary dressing 12 configured to be adhered to the patient in a conventional manner wherein the surface of the primary dressing to be adhered to the patient is fully covered by adhesive. The primary dressing 12 is configured to cover a catheter site 14 thereby inhibiting the catheter site 14 from being contaminated and inhibiting movement of the catheter relative to the patient. The primary dressing 12 has an outer perimeter edge 16. The outer perimeter edge 16 of the primary dressing 12 may be a geometric shape such as a square, rectangle, circle, oval, or the like. A cover dressing 18 has a central section 20 and a peripheral section 22. The central section 20 of the cover dressing 18 is transparent wherein the primary dressing 12 is visible when viewed through the central section 20. The central section 20 has a shape and size substantially equivalent to the primary dressing. This provides for full coverage of the primary dressing 12 by the cover dressing 18 while minimizing bulk.

A cover adhesive 24 is positioned on a lower surface 26 of the peripheral section 22 wherein the lower surface 26 of the peripheral section 22 is configured for adhering to the patient around the outer perimeter edge 16 of the primary dressing 12. Thus, the central section 20 extends over and covers the primary dressing 12 such that the cover dressing 18 prevents contamination of the primary dressing 12. The cover adhesive 24 is positioned on the lower surface 26 of the peripheral section 22 extending completely around the central section 20 wherein the cover dressing 18 is fully occlusive of the primary dressing 12. A lower surface 28 of the central section 20 is free from adhesive wherein the cover dressing 18 is prevented from adhering directly to the primary dressing 12. Thus, the primary dressing 12 is configured to remain in place over the catheter site 14 when the cover dressing 18 is removed from the patient. While specifically mentioned as applicable for the catheter site 14, it is to be understood the primary dressing 12 may alternatively cover a wound or any other site on the patient where bandaging would be desired. Each of a plurality of base markings 30 is positioned on a top surface 32 of the primary dressing 12. Each of the base markings 30 is positioned proximate to the outer perimeter edge 16 of the primary dressing 12. Each of the base markings 30 is continuously solid within an outermost border 34 of the base marking 30.

Each of a plurality of alignment markings 36 is positioned on the central section 20 of the cover dressing 18. Each of the alignment markings 36 corresponds to an associated one of the base markings 30 such that positioning the alignment markings 36 over the base markings 30 facilitates positioning of an interior edge 38 of the peripheral section 22 proximate to the outer perimeter edge 16 of the primary dressing 12. Placement in this manner defines a gap 40 between the interior edge 38 and the outer perimeter edge 16. The gap 40 has a consistent width extending fully around the primary dressing 12 when each of the alignment markings 36 is properly aligned with the associated one of the base markings 30. Each of the alignment markings 36 is a linear outline 42 complementary to the outermost border 34 of the associated one of the base markings 30. This allows continuity of visual contact with the base marking 30 as the associated alignment marking 36 is positioned over the base marking 30. Further, this arrangement provides for visible confirmation of proper alignment as misalignment will give the appearance of a bulge or offset in the shapes, or a gap between the linear outline 42 and the base marking 30 within the alignment marking 36. A shape of each of the base markings 30 and the alignment markings 36 is shown being circular but could be provided in other shapes.

In use, the cover dressing 18 is fully occlusive and protects the primary dressing 12. The cover dressing 18 can be removed if needed, such as by being contaminated by body fluids during a procedure. The cover dressing 18 is removed leaving the primary dressing 12 in tact and uncontaminated. The base markings 30 on the primary dressing 12 facilitate proper positioning of the cover dressing 18. This allows for less bulk, easier application of the cover dressing 18, and helps to insure the gap 40 as desired to prevent the cover dressing 18 from adhesively engaging the primary dressing 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A dual dressing catheter site covering system comprising:
a primary dressing being configured to be adhered to the patient, said primary dressing being configured to cover a catheter site thereby inhibiting said catheter site from being contaminated, said primary dressing having an outer perimeter edge;
a plurality of base markings positioned on a top surface of said primary dressing;
a cover dressing having a central section and a peripheral section, said central section of said cover dressing being transparent wherein said primary dressing is visible when viewed through said central section;
a cover adhesive positioned on a lower surface of said peripheral section wherein said lower surface of said peripheral section is configured for adhering to the patient around said outer perimeter edge of said primary dressing whereby said central section extends over and covers said primary dressing such that said cover dressing prevents contamination of said primary dressing; and
a plurality of alignment markings positioned on said central section, each of said alignment markings corresponding to an associated one of said base markings such that positioning said alignment markings over said base markings facilitates positioning of an interior edge of said peripheral section proximate to said outer perimeter edge of said primary dressing defining a gap between said interior edge and said outer perimeter edge.

2. The system of claim 1, further comprising a lower surface of said central section being free from adhesive wherein said cover dressing is prevented from adhering directly to said primary dressing whereby said primary dressing is configured to remain in place over the dressing site when said cover dressing is removed from the patient.

3. The system of claim 1, further comprising said central section having a shape and size equivalent to said primary dressing.

4. The system of claim 3, further comprising said primary dressing being visible through said central section.

5. The system of claim 1, further comprising said cover adhesive being positioned on said lower surface of said peripheral section extending completely around said central section wherein said cover dressing is fully occlusive of said primary dressing.

6. The system of claim 1, further comprising each of said base markings being positioned proximate to said outer perimeter edge of said primary dressing.

7. The system of claim 1, further comprising each of said base markings being continuously solid within an outermost border.

8. The system of claim 7 further comprising each of said alignment markings being a linear outline complementary to said outermost border of said associated one of said base markings.

9. The system of claim 8 further comprising a shape of each of said base markings and said alignment markings being circular.

10. The system of claim 1, further comprising said outer perimeter edge of said primary dressing being a geometric shape.

11. The system of claim 1, further comprising said gap having a consistent width extending fully around said primary dressing when each of said alignment markings is vertically aligned with said associated one of said base markings.

12. A dual dressing catheter site covering system comprising:
- a primary dressing being configured to be adhered to the patient, said primary dressing being configured to cover a catheter site thereby inhibiting said catheter site from being contaminated, said primary dressing having an outer perimeter edge, said outer perimeter edge of said primary dressing being a geometric shape;
- a cover dressing having a central section and a peripheral section, said central section of said cover dressing being transparent wherein said primary dressing is visible when viewed through said central section, said central section having a shape and size equivalent to said primary dressing; a cover adhesive positioned on a lower surface of said peripheral section wherein said lower surface of said peripheral section is configured for adhering to the patient around said outer perimeter edge of said primary dressing whereby said central section extends over and covers said primary dressing such that said cover dressing prevents contamination of said primary dressing, said cover adhesive being positioned on said lower surface of said peripheral section extending completely around said central section wherein said cover dressing is fully occlusive of said primary dressing;
- a lower surface of said central section being free from adhesive wherein said cover dressing is prevented from adhering directly to said primary dressing whereby said primary dressing is configured to remain in place over the dressing site when said cover dressing is removed from the patient;
- a plurality of base markings positioned on a top surface of said primary dressing, each of said base markings being positioned proximate to said outer perimeter edge of said primary dressing, each of said base markings being continuously solid within an outermost border; and
- a plurality of alignment markings positioned on said central section, each of said alignment markings corresponding to an associated one of said base markings such that positioning said alignment markings over said base markings facilitates positioning of an interior edge of said peripheral section proximate to said outer perimeter edge of said primary dressing defining a gap between said interior edge and said outer perimeter edge, said gap having a consistent width extending fully around said primary dressing when each of said alignment markings is vertically aligned with said associated one of said base markings, each of said alignment markings being a linear outline complementary to said outermost border of said associated one of said base markings, a shape of each of said base markings and said alignment markings being circular.

13. A dual dressing system, comprising:
- a primary dressing being configured to be adhered to the patient, the primary dressing being configured to cover a wound or other site on skin of the patient, thereby inhibiting the wound or the other site on the skin from being contaminated;
- a cover dressing having a transparent central section and a peripheral section, wherein the primary dressing is visible when viewed through the central section when the cover dressing is positioned relatively above the primary dressing, and wherein the peripheral section has a cover adhesive positioned thereon;
- the system configured such that when the primary dressing is positioned so to cover the wound or the other site on the skin, the cover dressing can be positioned over the primary dressing and secured to the patient by way of the cover adhesive positioned upon a peripheral section of the cover dressing such that the cover dressing completely surrounds a perimeter of the primary dressing; and
- the system further configured such that base markings present upon the primary dressing can be visually aligned with alignment markings present upon the transparent central section when positioning the cover dressing over the primary dressing.

14. The system of claim 13, further comprising a lower surface of the central section being free from adhesive wherein the cover dressing is prevented from adhering directly to the primary dressing whereby the primary dressing is configured to remain in place over the wound or the other site on the skin when the cover dressing is removed from the patient.

15. The system of claim 13, wherein the central section has a shape and size equivalent to or larger than the primary dressing.

16. The system of claim 13, further comprising the cover adhesive being positioned on the lower surface of the peripheral section extending completely around the central section wherein the cover dressing is fully occlusive of the primary dressing.

17. The system of claim 13, wherein each of the base markings are positioned proximate to the perimeter of the primary dressing.

18. The system of claim 13, wherein the perimeter has a geometric shape.

19. The system of claim 13, wherein a gap exists between the primary dressing and the peripheral section of the cover dressing when the cover dressing is positioned over the primary dressing.

\* \* \* \* \*